(12) United States Patent
Maizes

(10) Patent No.: US 6,175,751 B1
(45) Date of Patent: Jan. 16, 2001

(54) APPARATUS AND METHOD FOR SENSING OXYGEN LEVELS IN A FETUS

(75) Inventor: Allen Maizes, 6 Sassafras Ct., Scotch Plains, NJ (US) 07076

(73) Assignee: Allen Maizes, Scotch Plains, NJ (US)

( * ) Notice: Under 35 U.S.C. 154(b), the term of this patent shall be extended for 0 days.

(21) Appl. No.: 09/268,632

(22) Filed: Mar. 16, 1999

(51) Int. Cl.[7] .................................................... A61B 5/00
(52) U.S. Cl. ............................................................ 600/338
(58) Field of Search ................................... 600/310, 313, 600/322, 323, 338, 340, 341

(56) References Cited

U.S. PATENT DOCUMENTS

| | | |
|---|---|---|
| 5,057,695 * | 10/1991 | Hirao et al. ............................ 600/310 |
| 5,109,849 | 5/1992 | Goodman et al. . |
| 5,140,989 | 8/1992 | Lewis et al. . |
| 5,217,013 | 6/1993 | Lewis et al. . |
| 5,228,440 | 7/1993 | Chung et al. . |
| 5,349,961 | 9/1994 | Stoddart et al. . |
| 5,411,024 | 5/1995 | Thomas et al. . |
| 5,417,207 | 5/1995 | Young et al. . |
| 5,465,714 | 11/1995 | Scheuing . |
| 5,477,853 | 12/1995 | Farkas et al. . |
| 5,482,034 | 1/1996 | Lewis et al. . |
| 5,551,424 | 9/1996 | Morrison et al. . |
| 5,584,296 | 12/1996 | Cui et al. . |
| 5,632,273 | 5/1997 | Suzuki . |
| 5,738,901 | 4/1998 | Wang et al. . |
| 5,743,261 * | 4/1998 | Mainiero et al. ..................... 600/323 |
| 5,813,980 | 9/1998 | Levinson et al. . |
| 5,916,153 * | 6/1999 | Rhea, Jr. .............................. 600/310 |

OTHER PUBLICATIONS

Ramanujam, N. et al., Antepartum, Transabdominal Near Infrared Spectroscopy: Feasibility of Measuring Photon Migration Through the Fetal Head in Utero, The Journal of Maternal–Fetal Medicine, Nov.–Dec. 1999, 8:275–288.

Peebles, D.M., Neurologic Disorders in the Newborn, Clinics in Perinatology, Sep. 1997.

* cited by examiner

*Primary Examiner*—Eric F. Winakur
(74) *Attorney, Agent, or Firm*—Kenyon & Kenyon

(57) ABSTRACT

An apparatus for sensing fetal oxygen levels of a fetus in an uterus. The apparatus includes a tube, a balloon, and as optical sensor. The tube includes an inflation lumen. The inflation lumen has a distal end. The balloon is coupled to the distal end of the inflation lumen. The balloon includes a first membrane. The optical sensor unit is disposed on the first membrane.

21 Claims, 5 Drawing Sheets

APPARATUS AND METHOD FOR SENSING OXYGEN LEVELS IN A FETUS

BACKGROUND OF THE INVENTION

The present invention relates to an apparatus and method for sensing oxygen levels of a fetus.

During normal labor, the fetal head engages in the pelvis. Coincident with the mother pushing, uterine contractions, and dilatation of the cervix, the fetus is delivered.

In utero, the fetus receives its oxygen through the placenta. When the uterus contracts, the oxygen supply to the fetus is reduced until the uterus relaxes between contractions. In severe cases, this may result in fetal asphyxia, an impaired or absent exchange of oxygen and carbon dioxide on a ventilatory basis in the fetus. In extreme cases, fetal asphyxia may be associated with fetal cerebral injury.

Under the current standard of care, it is common for the heart rate of the fetus to be monitored during labor. In many instances, this fetal heart rate monitoring is performed through the cervix or the abdominal/uterine wall of the mother. Currently, the change in the fetus's heart rate relative to the uterine contractions is used to try to identify fetuses at risk. This current standard of care has been essentially, unsuccessful. "Current methods of intrapartum surveillance have made little impact in fetal mortality and morbidity while leading to increased caesarean section rates." Peoples, D. M., "Cerebral Hemodynamics and Oxygenation in the Fetus. The Role of Intrapartum near-infrared spectroscopy," Clinics in Perinatalogy September 1997 Vol. 24(3), pp. v. & 547–65. As a result research has been directed to better determine fetal oxygen levels.

One example of a known apparatus and method for sensing fetal oxygen levels is disclosed in U.S. Pat. No. 5,813,980 to Levinson et al., and assigned to Nellcor Puritan Bennett Incorporated. This method and apparatus is an optical method, which uses two wavelengths of light to determine the level of oxygen in pulsatile blood. This method is incapable of measuring fetal oxygen levels in non-pulsatile, or venous, blood.

U.S. Pat. No. 5,813,980 also teaches that there are two known types of fetal sensors: presenting part sensors and beyond the presenting part sensors. "Presenting part" refers to the region of the cervical os. "Beyond the presenting part" falls with in the uterus and extends out to the cervical os. Beyond the presenting part sensors can typically use the uterine wall to bias the sensor against the fetus. Presenting part sensors, on the other hand, cannot rely on the bias of the uterine wall, and may require positive attachment. Both known types of sensors, beyond the presenting part and presenting part, are placed through the cervix and require direct contact with fetal tissue. Since the sensor for both types must be placed in contact with fetal tissue, it interferes and partially obstructs the birth canal. Direct contact and interference with the fetus increases the risk of incidental injury to the fetal tissue from instrumentation and sensors. Further the protective amniotic fetal membranes would have to be ruptured to use this device. Finally, both known types of sensors can only be used when the fetal tissue is at or near the cervix. Thus, using either sensor it is not possible to measure the fetal oxygen level prior to labor.

In addition to monitoring the fetus, during labor, a catheter, typically a Foley catheter, is sometimes inserted into the mother's bladder for the purposes of evacuating urine. A Foley catheter inflates a balloon through an inflation lumen. The urine drains through the drainage lumen. The inflated Foley balloon keeps the catheter from sliding out of the bladder. Foley catheters are incapable of measuring fetal oxygen levels or other parameters. Thus, using previously known methods, to simultaneously evacuate urine and monitor fetal oxygen levels required the use of at least two separate devices.

SUMMARY OF THE INVENTION

The present invention provides an apparatus for sensing fetal oxygen levels of a fetus in a uterus. A tube includes an inflation lumen. The inflation lumen has a distal end. A balloon is coupled to the distal end of the inflation lumen. The balloon includes a first membrane. An optical sensor is disclosed on the first membrane.

Another aspect of the present invention provides a method for sensing fetal oxygen levels of a fetus in a uterus. The uterus has a wall and is adjacent to a body cavity. An optical sensor is inserted into the body cavity. The optical sensor includes a wall. The wall of the optical sensor is oriented substantially towards the fetus. The oxygen levels of the fetus are measured with the optical sensor through the wall of the uterus.

DETAILED DESCRIPTION

Figure 1:
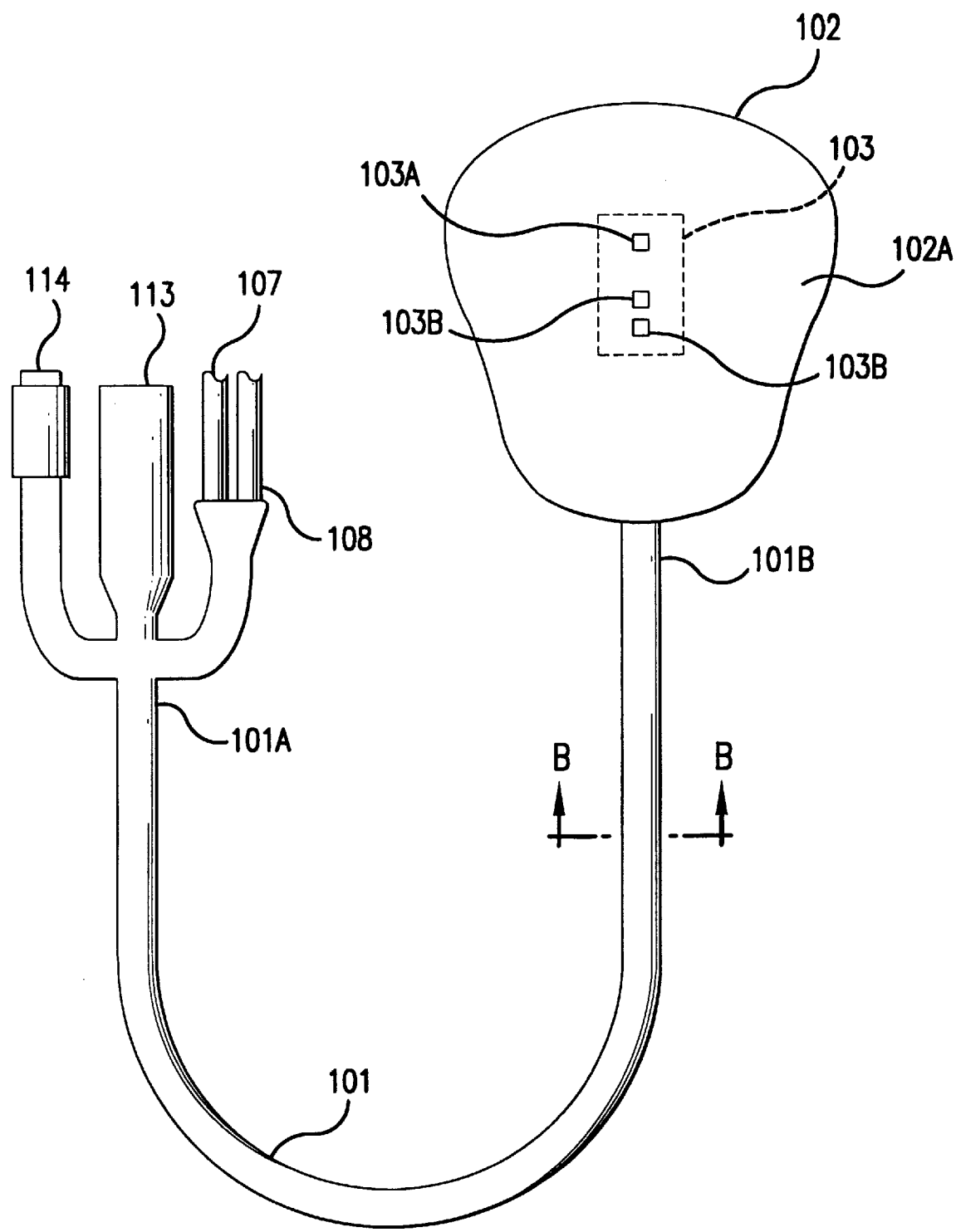
FIG. 1 is a front plan view of one embodiment of the invention including a balloon disposed on the distal end of a tube.

FIG. 1 illustrates the front view of one embodiment of the present invention. Tube 101 has proximal end 101A and distal end 101B. Tube 101 may be constructed of a flexible material, such as a silicone elastomer. In the embodiment illustrated in FIG. 1, construction of proximal end 101A is similar to that of a Foley catheter.

Balloon 102 is coupled—either directly or indirectly—to distal end 101B. Balloon 102 may be constructed of a number of flexible materials, such as a surgical grade silicone. Balloon 102 is an inflatable member, and has an inflated configuration and a deflated configuration. The shape of balloon 102 in its inflated configuration is illustrated in FIGS. 1–4. Those skilled in the art will understand that the inflated configuration is not limited to the inflated configuration illustrated in FIG. 1. In FIG. 1, the inflated configuration of balloon 102 is shaped to conform to the interior of the uterine bladder during labor. The inflated configuration is curved to approximate the curvature of the head of a fetus. The balloon 102 may include a fetal-oriented wall 102A, which is concave, and a non-fetal-oriented wall 102B (not visible in FIG. 1), which is convex.

It should also be noted that the fetal-oriented wall 102A and the non-fetal-oriented wall 102B of the balloon 102 may either be integrally formed or disparate. For instance, the balloon 102 could be integrally molded as a continuously formed piece of silicone. In other instances, it may be desirable to manufacture fetal-oriented wall 102A and non-fetal-oriented wall 102B separately and then adhere them to each other during the manufacturing process.

In one embodiment, optical sensor 103 is disposed on fetal-oriented wall 102A. In one embodiment, optical sensor 103 includes a planar-shaped body having a soft, resilient outer cover on at least one side, an electro-optical light source 103A, and a plurality of electro-optical light detectors 103B. The optical sensor 103 includes a contacting side and a non-contacting side. The optical sensor 103 is disposed on the fetal-oriented wall 102A so that the contacting side faces substantially toward the exterior of the balloon 102 and the non-contacting side faces substantially toward the interior of the balloon 102. Known optical sensors 103 are disclosed in U.S. Pat. Nos. 5,217,013 and 5,632,273, both of which are incorporated herein by reference. Those skilled in the art will understand that optical sensor 103 includes any sensor that is capable of sensing the levels of oxygen in tissue, and not limited to the optical sensor disclosed in U.S. Pat. Nos. 5,217,013 and 5,632,273. It is also to be noted that the term "disposed on the fetal-oriented wall" include configurations where optical sensor 103 is coupled to the interior of fetal-oriented wall 102A, the exterior of fetal-oriented wall 102A, and/or within fetal-oriented wall 102A (i.e., impregnated within the wall of the balloon 102).

As further illustrated in the embodiment of FIG. 1, drainage outlet 113 is disposed on proximal end 102A, fluid inlet 114 is disposed on proximal end 114. Light source conduit 105 and optical sensor conduit both exit from the proximal end 102A.

Figures 2, 3:
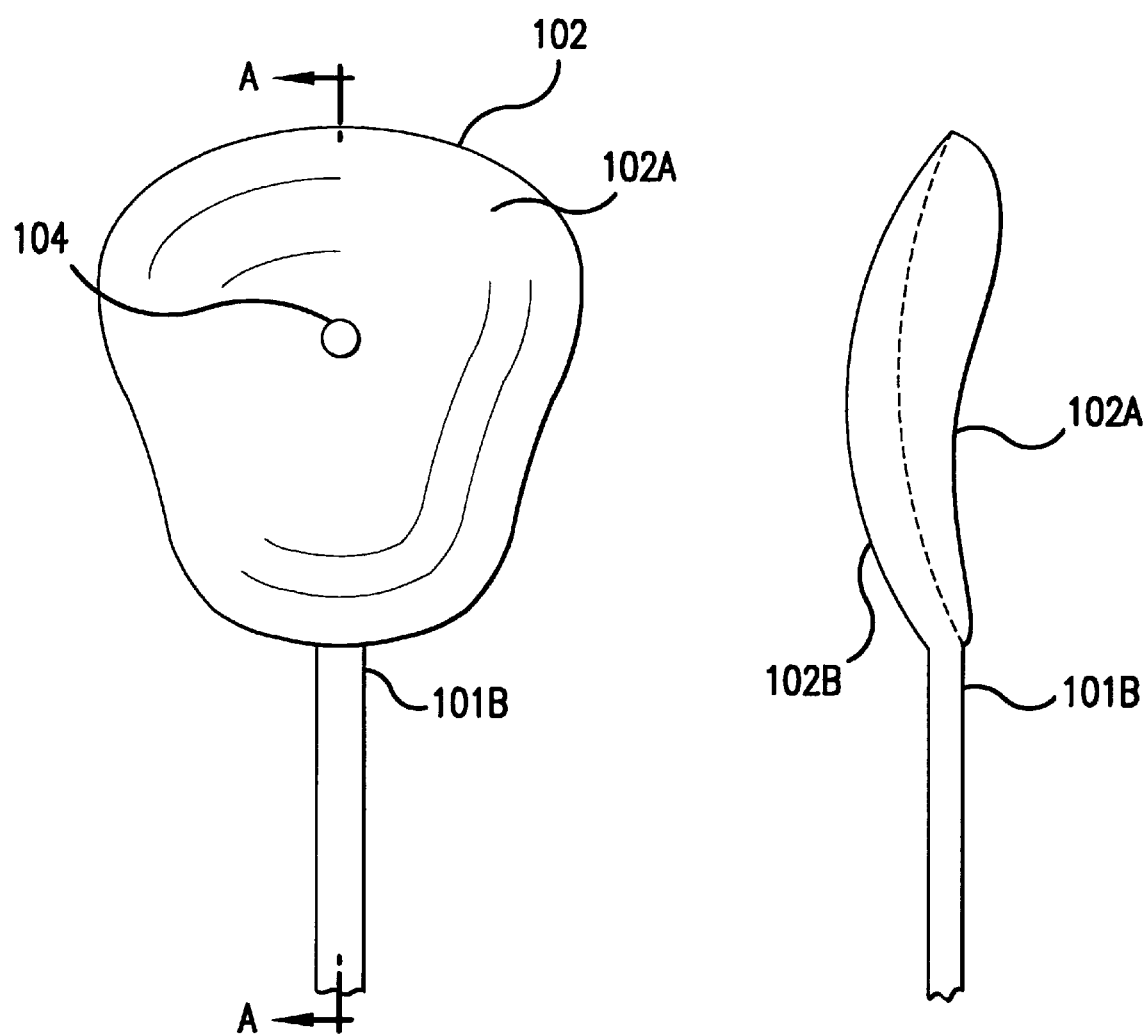
FIG. 2 is a rear plan view of the balloon in the embodiment of FIG. 1.
FIG. 3 is a side elevational view of the balloon in the embodiment of FIG. 1.

FIG. 2 is a rear plan view of balloon 102. Position indicator 104 is disposed on non-fetal-oriented wall 102B. In the embodiment illustrated in FIG. 2, position indicator 104 is a light source, however, position indicator 104 may be any device and/or indicator that communicates the orientation of balloon 102. An example of other position indicators 104 are external markers. The light source may be substantially unidirectional, such as the terminus of a fiber optic cable, a light emitting diode (LED), or a semiconducting laser. The light source is directed substantially outward to the exterior of balloon 102, or a direction normal and outward to the fetal-oriented wall 102A. The position indicator may be coupled to the interior of the non-fetal-oriented wall 102B, the exterior of the non-fetal-oriented wall 102B, and/or within the non-fetal-oriented wall 102A (i.e., impregnated within the wall of the balloon).

FIG. 3 illustrates a side elevational view of balloon 102. As illustrated in FIG. 3, non-fetal-oriented wall 102B is substantially convex and fetal-oriented wall 102A is substantially concave.

Figure 4:
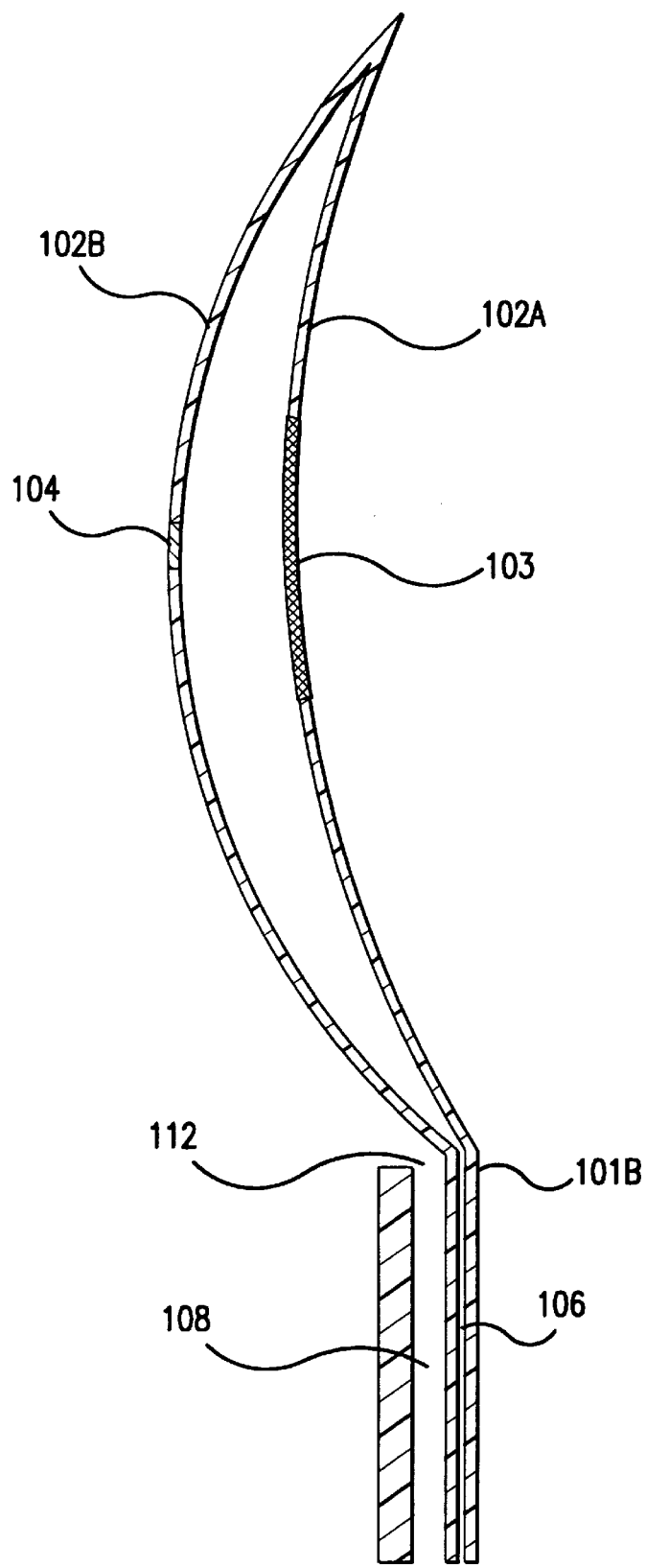
FIG. 4 is an enlarged cross-sectional view taken along plane A—A of FIG. 2.

FIG. 4 illustrates an enlarged cross-sectional view of balloon 102 along section A—A of FIG. 2. Fetal-oriented wall 102A and non-fetal-oriented wall 102B form balloon 102. Optical sensor 103 is disposed on fetal-oriented wall 102A and position indicator 104 is disposed on non-fetal-oriented wall 102B. Balloon 102 communicates with inflation lumen 106. Drainage inlet 112 is disposed at the interface between distal end 101B and balloon 102. In the illustrated embodiment, drainage lumen 108 communicates between drainage inlet 112 and drainage outlet 113.

Figure 5:
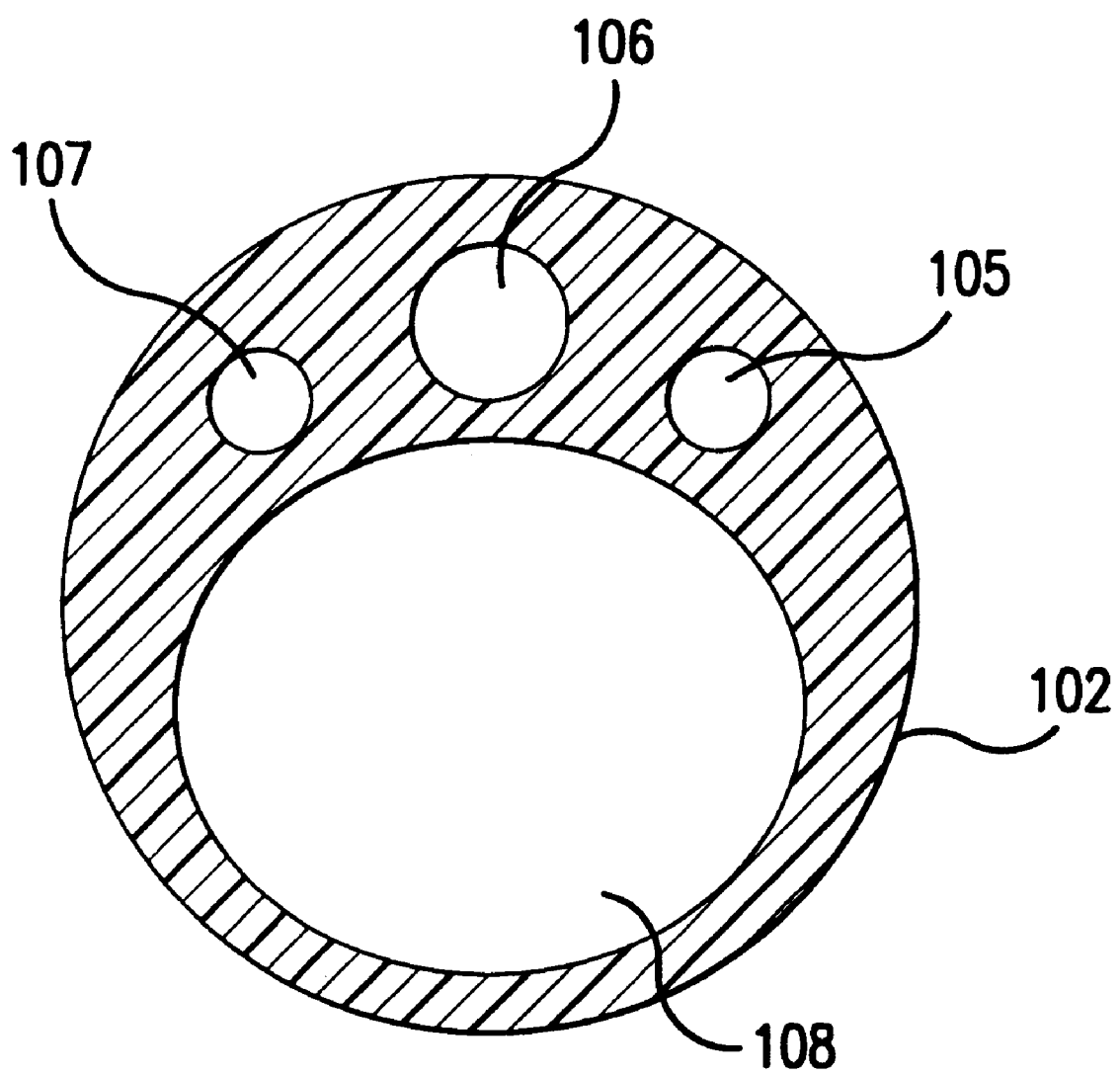
FIG. 5 is a cross-sectional view taken along plane B—B of FIG. 1.

FIG. 5 is a cross-sectional view taken along plane B—B of FIG. 1. The cross section illustrated in FIG. 5 is a typical cross section of tube 101 except for the portions near proximal end 101A and distal end 101B. Encased within tube 101 are drainage lumen 108, inflating lumen 106, light source conduit 107, optical sensor conduit 105. It should also be noted that the bundling of the light source conduit 107, inflating lumen 106, conduit 105, and drainage lumen 108 need not be bundled in a common tube 101. For instance, it may be desirable to separate each of these conduits and lumens for manufacturing and/or use purposes. In certain instances, however, it may be desirable to bundle all of these functions in a single tube 101. This minimizes the number of individual conduits that are inserted into the body cavity and prevents tangling of the conduits during measurement.

Figure 6:
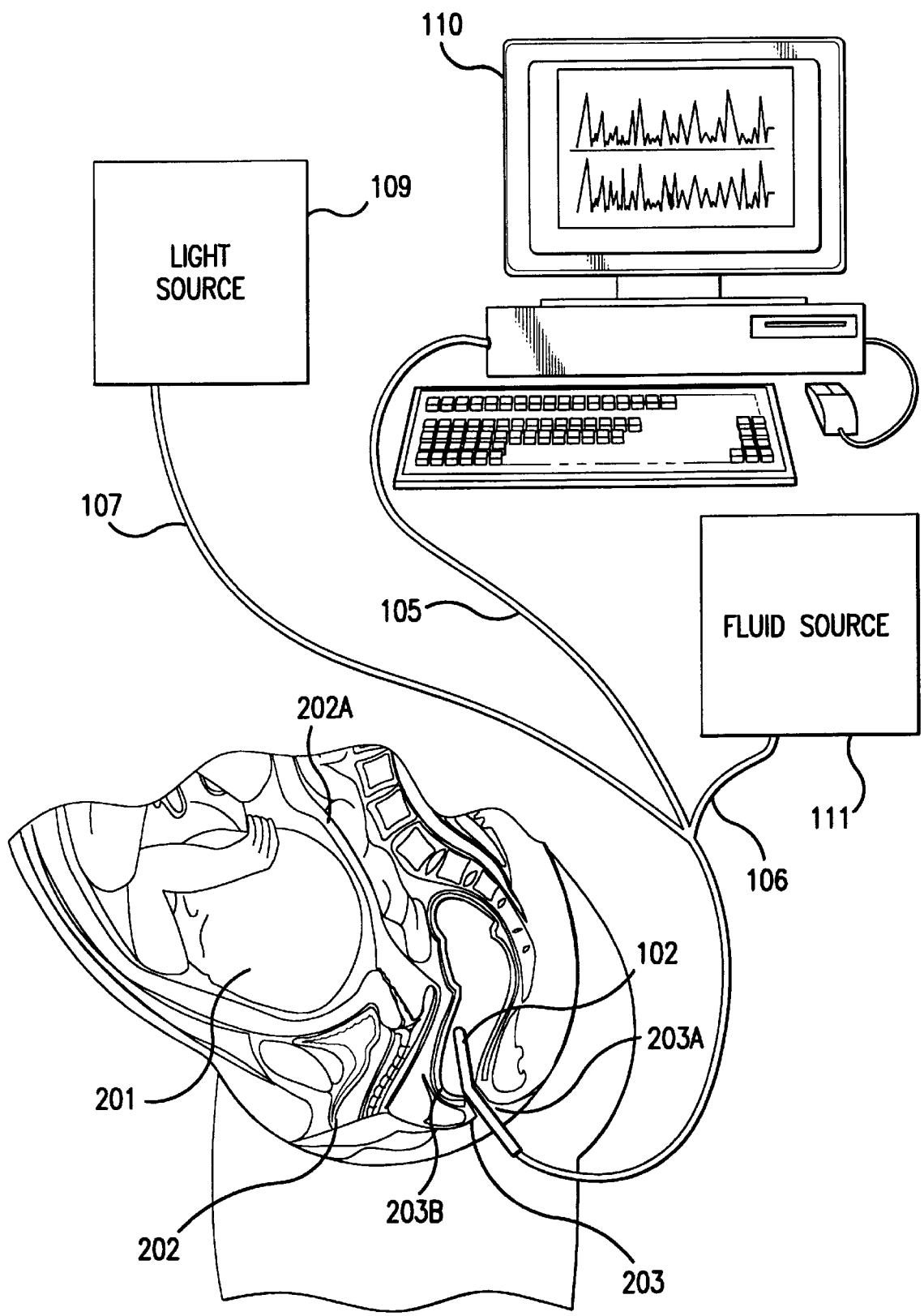
FIG. 6 is a schematic representation illustrating a typical environment for the apparatus in accordance with the present invention.

FIG. 6 is a schematic representation illustrating a typical environment for the apparatus in accordance with the present invention. Light source 109 is any source that provides light to the position indicator 104. For instance, light source 109 may be a fiber optic source, when position indicator the terminus of a fiber optic cable, or an electrical source, when the position indicator is an LED. Light source conduit 107 communicates between position indicator 104 and light source 109.

Fluid source 111 may be any source that provides a fluid. For instance, fluid source may be a syringe or a pump. The fluid used may be a liquid, such as saline, water, or a gel, or a gas, such as air. Inflating lumen 106 communicates between balloon 102 and fluid source 111.

Control unit 110 is a unit that sends and receives signals from optical sensor 103. One control unit is described in U.S. Pat. No. 5,482,034, which is incorporated herein by reference. Electro-optic conduit 105 communicates between optical sensor 103 and control unit 110.

FIG. 6, further illustrates the approximate anatomy of a human female during labor. Fetus 201 is shown in a head-down position. Fetus 201 is encased by the uterus 202, which includes uterine wall 202A. Adjacent to uterine wall 202A is body cavity 203, which includes body cavity opening 203A and body cavity wall 203B. For the purposes of this invention, the body cavity may include any cavity or tissue that is substantially adjacent to the uterus 202 or uterine wall 202A, such as a urinary bladder, vagina, and rectum. As with other illustrations, body cavity 203 is not illustrated anatomically or proportionally, but intended to illustrate the relative position in relation to the uterus 202.

In one embodiment of the present invention, fetal oxygen levels are measured according to the following process.

Balloon 102 is deflated to its deflated configuration. This may be performed by applying a negative pressure to the fluid source 111. The deflation reduces the overall package size that will be inserted into the body cavity. In certain embodiments, it may be desirable to deflate the balloon to a predetermined deflated configuration, such as a spiral or scroll configuration. Methods for deflating the balloon to a predetermined configuration may include the use of a memory metal frame that retracts the balloon to a deflated configuration. In addition, polymer coatings similar to those disclosed in U.S. Pat. No. 5,738,901, which is incorporated herein by reference, may cause the balloon to prefer a predetermined configuration. In other embodiments, it may be desirable to deflate the balloon 102 and retract balloon 102 into a working lumen (not shown).

After deflating the balloon, balloon 102 is inserted into body cavity 203 through body cavity opening 203A. To reduce the risk of infection, the insertion usually occurs under sterile conditions.

At some point after insertion, balloon 102 is oriented so that contacting surface of optical sensor 103 is directed towards the fetus. One method for orienting includes engaging light source 109 to provide position indicator 104 with light via light source conduit 107. As noted above, position indicator 104 is on the opposite side of balloon 102 that optical sensor 103 is disposed. Orientation includes the acts of rotating the tube 101 until the position indicator 104 is visible through the body cavity wall 203B. For instance, when body cavity 203B is a urinary bladder, it is known that proximal wall of the urinary bladder and the adjacent pubes is relatively thin during labor. The position indicator is thus visible externally through the bladder wall and the pubes. When the position indicator is observed through the pubes, this indicates that the optical sensor 103 is likely facing the fetus 201.

At some point after insertion, balloon 102 is inflated by providing a fluid from fluid source 111 via inflating lumen 106. When the balloon 102 is inflated, it occupies volume which would otherwise be occupied by urine in the urinary bladder 203. This evacuates the urine that is in the urinary bladder 203. The urine is evacuated through the drainage lumen 108 via the eye opening 112. It should be noted that this inflation of the balloon 102 serves the same purpose that a Foley catheter would during a normal labor operation. Foley catheters are typically used to evacuate urine prior to labor during birth. Thus, the present invention combines the features of both a Foley catheter and introduces a fetal oximeter that monitors the oxygen levels of the fetus during birth.

The concave shape of the fetal-oriented wall 102A conforms to the shape of the fetus' head. Balloon 102 is also made to contact with body cavity wall 203B due to the flattening of body cavities 203 at or near labor. For instance, it is known that the urinary bladder becomes flattened as the contractions occur and the water breaks in the mother. The bladder flattens even more when the cervix is dilated. The combination of the flattening effect and the curved shape of balloon 102 ensures that optical sensor 103 will contact body cavity wall 203A adjacent to uterus 202. It should be noted that either the inflation step or the orientation step may occur first.

The process also includes the step of monitoring the fetal oxygen levels of the fetus 201. These oxygen levels may be monitored throughout the entire birthing process. Optical sensor 103 measures the levels of oxygen in fetus 201 through the body cavity wall 203A and uterine wall 202A. Methods for measuring oxygen levels in adult patients are discussed in U.S. Pat. Nos. 5,217,013 and 5,632,273, both of which are incorporated herein by reference. Those skilled in the art will understand that these methods may be modified to measure the levels of oxygen in fetus 201 through the uterine wall 202A and the body cavity wall 203A.

The present invention illustrates an embodiment that is applicable for use in the urinary bladder. In other instances, however, it may be unnecessary to include balloon 102. For instance, when applying the optical sensor to the vagina to measure the oxygen levels of the fetus through the cervix, there is no need for balloon 102. In such instances, the optical sensor may be simply inserted near the proximity of the cervix via the vagina.

In addition to monitoring fetal oxygen levels, the present invention is capable of measuring fetal heart rates and uterine contractions. Fetal heart rates may be monitored using fetal heart rate sensors (not shown), such as pulse Doppler ultrasound sensors. The fetal heart rate sensor may be disposed on the surface of the balloon 102. Uterine pressure may be monitored using uterine pressure sensors (not shown), such as toconometer sensors. The uterine pressure sensor may be disposed on the surface of the balloon 102.

What is claimed is:

1. An apparatus for sensing oxygen levels of a fetus in a uterus having a uterine wall, comprising:
    a tube including an inflation lumen, said inflation lumen having a distal end;
    a balloon coupled to the distal end of said inflation lumen, said balloon including a first membrane; and
    an optical sensor unit disposed on the first membrane and capable of sensing the oxygen levels of the fetus through the uterine wall and a body cavity wall.

2. The apparatus of claim 1, wherein said tube further includes a drainage lumen having an opening substantially adjacent to said balloon.

3. The apparatus of claim 1, wherein the balloon is made of an elastomeric material.

4. The apparatus of claim 1, wherein the balloon is made of silicone.

5. The apparatus of claim 1, wherein the optical sensor further includes:
    a source;
    a first receiver; and
    a second receiver.

6. The apparatus of claim 1, wherein said balloon has an inflated configuration, the first membrane having a substantially concave exterior wall in the inflated configuration, and a second membrane having a substantially convex exterior wall in the inflated configuration.

7. The apparatus of claim 1, further comprising:
    a fetal heart rate sensor disposed on the first membrane.

8. The apparatus of claim 1, further comprising:
    a uterine contraction sensor disposed on the first membrane.

9. An apparatus for sensing fetal oxygen levels of a fetus in a uterus, comprising:
    a tube including an inflation lumen, said inflation lumen having a distal end;
    a balloon coupled to the distal end of said inflation lumen, said balloon including a first membrane and a retraction coating disposed on the exterior wall of said balloon, wherein the retraction coating is set while the balloon is in the deflated configuration; and
    an optical sensor unit disposed on the first membrane.

10. The apparatus of claim 9, wherein the retraction coating is a shape memory polymer.

11. An apparatus for sensing fetal oxygen levels of a fetus in a uterus, comprising:
    a tube including an inflation lumen, said inflation lumen having a distal end;
    a balloon coupled to the distal end of said inflation lumen, said balloon including:
        a first membrane;
        a retraction frame; and
        an optical sensor unit disposed on the first membrane.

12. An apparatus for sensing fetal oxygen levels of a fetus in a uterus, comprising:
    a tube including an inflation lumen, said inflation lumen having a distal end;
    a balloon coupled to the distal end of said inflation lumen, said balloon including a first membrane and a second membrane, said second membrane having a position indicator, a portion of the position indicator being disposed on the second membrane; and an optical sensor unit disposed on the first membrane.

13. The apparatus of claim 12, wherein the second membrane has an exterior wall and wherein the position indicator is a light source directed substantially outward to the exterior wall.

14. A catheter-oximeter, comprising:
  a tube including an inflation lumen and a drainage lumen, the drainage lumen communicating with a drainage inlet
  a balloon including a first wall and a second wall, said balloon communicating with the inflation lumen;
  an optical sensor disposed on the first wall; and
  a position indicator disposed on the second wall.

15. A method for sensing oxygen levels of a fetus in a uterus, the uterus having a uterine wall and being substantially adjacent to a body cavity having a body cavity wall, comprising the steps of:
  inserting an optical sensor into the body cavity, said optical sensor having a wall;
  orienting the wall of the optical sensor substantially towards the fetus; and
  measuring the oxygen levels of the fetus with the optical sensor through the uterine wall and the body cavity wall.

16. The method of claim 15, wherein the optical sensor is disposed on a balloon, further comprising the of:
  inflating the balloon with a fluid.

17. The method of claim 15, wherein said inflating step occurs after said inserting step.

18. The method of claim 15, wherein the body cavity is a urinary bladder.

19. The method of claim 15, wherein the body cavity is a rectum.

20. The method of claim 15, wherein the body cavity is a vagina.

21. A method for sensing fetal oxygen levels of a fetus in a uterus, the uterus having a wall and being adjacent to the pubes, comprising the steps of:
  inserting an optical sensor into the body cavity, said optical sensor having a wall;
  providing a light source in a direction substantially opposite to the outward normal of the wall of the optical sensor;
  rotating the optical sensor;
  detecting the light source on the surface of the pubes; and
  measuring the oxygen levels of the fetus with the optical sensor through the wall of the uterus.

* * * * *

UNITED STATES PATENT AND TRADEMARK OFFICE
CERTIFICATE OF CORRECTION

PATENT NO. : 6,175,751 B1
DATED : January 16, 2001
INVENTOR(S) : Allen Maizes

It is certified that error appears in the above-identified patent and that said Letters Patent is hereby corrected as shown below:

Title page,
Delete "(73) Assignee: Allen Maizes, Scotch Plains, NJ (US)"

Signed and Sealed this

Thirty-first Day of July, 2001

*Attest:*

*Attesting Officer*

NICHOLAS P. GODICI
*Acting Director of the United States Patent and Trademark Office*